United States Patent
Matsumiya et al.

(10) Patent No.: US 11,234,670 B2
(45) Date of Patent: Feb. 1, 2022

(54) MEASURING X-RAY CT APPARATUS AND TOMOGRAPHIC IMAGE GENERATING METHOD

(71) Applicant: MITUTOYO CORPORATION, Kanagawa (JP)

(72) Inventors: Sadayuki Matsumiya, Kanagawa (JP); Hidemitsu Asano, Kanagawa (JP); Masato Kon, Kanagawa (JP)

(73) Assignee: MITUTOYO CORPORATION, Kanagawa (JP)

( * ) Notice: Subject to any disclaimer, the term of this patent is extended or adjusted under 35 U.S.C. 154(b) by 87 days.

(21) Appl. No.: 16/291,674

(22) Filed: Mar. 4, 2019

(65) Prior Publication Data
US 2019/0274654 A1   Sep. 12, 2019

(30) Foreign Application Priority Data

Mar. 12, 2018 (JP) .............................. JP2018-044643

(51) Int. Cl.
*G06K 9/00* (2006.01)
*A61B 6/00* (2006.01)
(Continued)

(52) U.S. Cl.
CPC .............. *A61B 6/584* (2013.01); *A61B 6/032* (2013.01); *G01N 23/046* (2013.01); *G06T 11/005* (2013.01)

(58) Field of Classification Search
CPC ................ G01N 23/046; G06T 11/005; G06T 2211/421; G06T 2211/416;
(Continued)

(56) References Cited

U.S. PATENT DOCUMENTS 5,640,436 A * 6/1997 Kawai .................. G06T 11/005
378/4
2004/0258197 A1* 12/2004 Goto ...................... A61B 6/032
378/19
(Continued)

FOREIGN PATENT DOCUMENTS

JP         2002-071345 A      3/2002
JP         2004-012407 A      1/2004
WO    WO-2017141345 A1 *   8/2017    ........... G01N 23/044

OTHER PUBLICATIONS

U.S. Appl. No. 16/299,513 to Kozo Ariga et al., which was filed Mar. 12, 2019.
(Continued)

*Primary Examiner* — Atiba O Fitzpatrick
(74) *Attorney, Agent, or Firm* — Greenblum & Bernstein, P.L.C.

(57) ABSTRACT

When generating a tomographic image using a measuring X-ray CT apparatus that is configured to emit X-rays while rotating a specimen that is arranged on a rotary table and reconstruct a projection image thereof to generate a tomographic image of the specimen, an amount of geometric error that is included in the projection image is obtained in advance and stored; the projection image is corrected using the stored amount of geometric error; and a tomographic image is reconstructed using the corrected projection image.

6 Claims, 14 Drawing Sheets

(51) Int. Cl.
*G01N 23/046* (2018.01)
*G06T 11/00* (2006.01)
*A61B 6/03* (2006.01)

(58) Field of Classification Search
CPC ........... G06T 2211/424; G06T 2211/40; G06T 2207/10081; G06T 2207/10072; G06T 2207/10088; G06T 2211/428; A61B 6/032
See application file for complete search history.

(56) References Cited

U.S. PATENT DOCUMENTS

| | | | |
|---|---|---|---|
| 2005/0046644 A1* | 3/2005 | Ohishi | A61B 6/504 345/643 |
| 2005/0272993 A1* | 12/2005 | Ishii | G06T 11/005 600/407 |
| 2006/0262896 A1* | 11/2006 | Nishide | A61B 6/469 378/15 |
| 2007/0122020 A1* | 5/2007 | Claus | A61B 6/583 382/131 |
| 2011/0123088 A1* | 5/2011 | Sebok | G06T 11/005 382/132 |
| 2011/0228906 A1* | 9/2011 | Jaffray | A61B 6/032 378/65 |
| 2016/0022241 A1* | 1/2016 | Guntzer | A61B 6/482 378/62 |
| 2016/0305894 A1* | 10/2016 | Matsumiya | G01N 23/046 |
| 2018/0120242 A1* | 5/2018 | Takahashi | G01B 21/02 |

OTHER PUBLICATIONS

U.S. Appl. No. 16/250,167 to Kozo Ariga et al., which was filed Jan. 17, 2019.
U.S. Appl. No. 16/291,699 to Hidemitsu Asano et al., which was filed Mar. 4, 2019.
U.S. Appl. No. 16/250,201 to Hidemitsu Asano et al., which was filed Jan. 17, 2019.

* cited by examiner

Ideal projection image

Projection image when rotary table has eccentricity or surface tilt

Projection image

Rotation about Z axis

Rotation about Y axis

MEASURING X-RAY CT APPARATUS AND TOMOGRAPHIC IMAGE GENERATING METHOD

CROSS-REFERENCE TO RELATED APPLICATIONS

The present application claims priority under 35 U.S.C. § 119 of Japanese Application No. 2018-044643, filed on Mar. 12, 2018, the disclosure of which is expressly incorporated by reference herein in its entirety.

BACKGROUND OF THE INVENTION

1. Field of the Invention

The present invention relates to a measuring X-ray CT apparatus and to a tomographic image generating method. In particular, the present invention relates to a measuring X-ray CT apparatus and to a tomographic image generating method that are capable of generating a highly accurate tomographic image regardless of an amount of geometric error in the eccentricity of a rotation axis of a rotary table, surface tilt of the table, or similar.

2. Description of Related Art

Medical X-ray CT apparatuses were brought into practical use in the 1970s, and based on this technology, X-ray CT apparatuses for industrial products came out around the early 1980s. Since then, industrial X-ray CT apparatuses have been used for observation and inspection of pores in cast metal components, a welding issue of a welded component, a circuit pattern defect of an electronic circuit component, and the like, which are difficult to check from an external view. Meanwhile, along with a recent spread of 3D printers, demand is growing not only for the observation and inspection of the interior of work pieces created by 3D printers, but also for 3D dimension measurement of internal structures, and for increased accuracy thereof.

With respect to the above-mentioned trends in the technology, the measuring X-ray CT apparatus has begun spreading in areas centering on Germany (See Japanese Patent Laid-open Publication Nos. 2002-71345 and 2004-12407). In the measuring X-ray CT apparatus, a measured object is placed at the center of a rotary table and X-ray irradiation is performed while rotating the measured object.

A configuration of a generic X-ray CT apparatus 1 which is used for measurement is shown in FIG. 1. The X-ray CT apparatus 1 is configured with an enclosure 10 which shields X-rays, a controller 20, a control PC 22, and the like. The enclosure 10 includes therein: an X-ray source 12 emitting X-rays 13 (shaped in a cone beam), an X-ray detection device 14 detecting the X-rays 13, a rotary table 16 on which a specimen W is placed and which rotates the specimen W for CT imaging, and an XYZ displacement mechanism 18 adjusting a position or magnification ratio of the specimen W which is projected onto the X-ray detection device 14. The controller 20 controls the devices mentioned above, and the control PC 22 issues instructions from, e.g., a user operation to the controller 20.

In addition to controlling each device, the control PC 22 includes a function to display on a screen or other type of monitor a projection image of the specimen W which is projected onto the X-ray detection device 14, and a function to reconstruct a tomographic image from a plurality of projection images of the specimen W.

As shown in FIG. 2, the X-rays 13 fired or emitted from the X-ray source 12 reach the X-ray detection device 14 by passing through the specimen W on the rotary table 16. The tomographic image of the specimen W is generated by obtaining, with the X-ray detection device 14, transmission images (projection images) of the specimen W in various directions while rotating the specimen W and by reconstructing the images using a reconstruction algorithm, such as a back projection method, a successive approximation method, and the like.

By controlling XYZ axes of the XYZ displacement mechanism 18 and a θ axis of the rotary table 16, the position of the specimen W can be shifted and an image capture range (position, magnification ratio) or an image capture angle of the specimen W can be adjusted.

In order to acquire a tomographic image or volume data (stereoscopic image or aggregation of tomographic images in the Z axis direction) of the specimen W, which is the ultimate objective of the X-ray CT apparatus 1, a CT scan of the specimen W is performed.

A CT scan is composed of two processes: acquiring a projection image of the specimen W and CT reconstruction. In the projection image acquisition process, the rotary table 16 on which the specimen W rests during X-ray irradiation is rotated continuously at a fixed speed or intermittently by fixed step widths, and a projection image of the specimen W is acquired in the entire circumferential direction (a fixed interval). The resulting projection image for the entire circumferential direction (fixed interval) undergoes CT reconstruction using a CT reconstruction algorithm such as a back projection method or a successive approximation method, thereby obtaining, as exemplified in FIG. 3, a tomographic image or volume data for the specimen (master balls in FIG. 3).

Broadly speaking, CT reconstruction algorithms may be broken into the classes of back projection methods and successive approximation methods.

As exemplified in FIG. 4, a back projection method creates a back projection of a projection image on a running basis, from a projection direction in which the image was acquired.

As exemplified in FIG. 5, a successive approximation method uses calculations to find a projection image from an estimated image of the specimen, and repeatedly revises the image of the specimen so that the projection image approaches an actual projection image.

The back projection method and successive approximation method may be more finely divided into numerous algorithms, but all of these algorithms are predicated on a projection image being acquired with correct alignment.

As described above, a rotary table is used to rotate the specimen, but when the rotary table used during a CT scan has eccentricity in a rotation axis or surface tilt, the effects of this are incorporated into the projection image acquired at each rotation angle, and this effect manifests as an artifact in the tomographic image obtained through CT reconstruction.

For example, in a back projection method, when a projection position of one projection image is offset due to a positioning error of the rotary table, a back projection of the projection image is created at the wrong position and inconsistencies appear in the CT reconstruction calculation. Also, in a successive approximation method, the method approaches a projection image that contains errors.

The following two parameters are indicators that can confirm whether a projection image is acquired with the correct alignment.

(1) Rotation axis: The rotation axis of the specimen.

(2) Scan axis: The scan position when one sectional image is generated. This position forms an axis that passes through a point where X-rays intersect orthogonally with an X-ray detection device (ideally at the center of the X-ray detection device), and that is orthogonal to the rotation axis. This is also a consideration with CT reconstruction algorithms when generating volume data.

As illustrated in FIG. 6, in order to perform highly accurate CT reconstruction, projection images of the rotation axis and the scan axis described above must coincide in the projection images for the entire circumferential direction, and must match those positions on which the CT reconstruction algorithm is predicated.

With the above-noted principles of CT reconstruction, when a rotary table has eccentricity in a rotation axis as illustrated in FIG. 7, or has surface tilt as illustrated in FIG. 8, an actual rotation axis and scan axis do not coincide with the calculated axes. Furthermore, when the eccentricity and surface tilt change due to the rotation angle of the rotary table, the projection images of the rotation axis and scan axis differ throughout the projection image for the entire circumferential direction and CT reconstruction is not accurate.

When the specimen image in the projection image diverges from the calculated position in this way, not only does the specimen image in the tomographic image and volume data generated by the CT reconstruction become blurry, but as illustrated in FIG. 9, a significant amount of noise (which includes false images) may occur in the specimen image, the CT reconstruction calculation may fail, and so on.

SUMMARY OF THE INVENTION

The present invention has been conceived in light of the conventional circumstances above and in cases where an amount of geometric error such as eccentricity in a rotation axis and surface tilt of a rotary table can be obtained ahead of time, the present invention seeks to generate a highly accurate tomographic image by using the geometric error to correct a projection image directly.

The present invention addresses this challenge by equipping a measuring X-ray CT apparatus that is configured to emit X-rays while rotating a specimen that is arranged on a rotary table and to reconstruct a projection image thereof to generate a tomographic image of the specimen with: a memory storing an amount of geometric error that is obtained in advance and that is included in the projection image; a corrector using the stored amount of geometric error to correct the projection image; and a reconstructor using the corrected projection image to reconstruct a tomographic image.

In this example, the amount of geometric error can be eccentricity or surface tilt of the rotary table.

In addition, when generating a tomographic image using a measuring X-ray CT apparatus that is configured to emit X-rays while rotating a specimen that is arranged on a rotary table and reconstruct a projection image thereof to generate a tomographic image of the specimen, an amount of geometric error that is included in the projection image can be obtained in advance and stored; the projection image can be corrected using the stored amount of geometric error; and a tomographic image can be reconstructed using the corrected projection image.

According to the present invention, highly accurate tomographic images and volume data can be generated by using a known amount of geometric error, such as eccentricity or surface tilt of a rotary table, to correct a projection image directly.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, embodiments of the present invention are described in detail with reference to the drawings. Moreover, the present invention is not limited by the content described in the embodiments and examples that follow. Additionally, elements easily conceivable to a person skilled in the art and elements that are intrinsic equivalents or otherwise equal in scope are included within the compositional requirements of the examples and the embodiments below. Furthermore, the disclosed compositional requirements within the written embodiments and examples below may be combined or selectively employed as appropriate.

Figure 10:
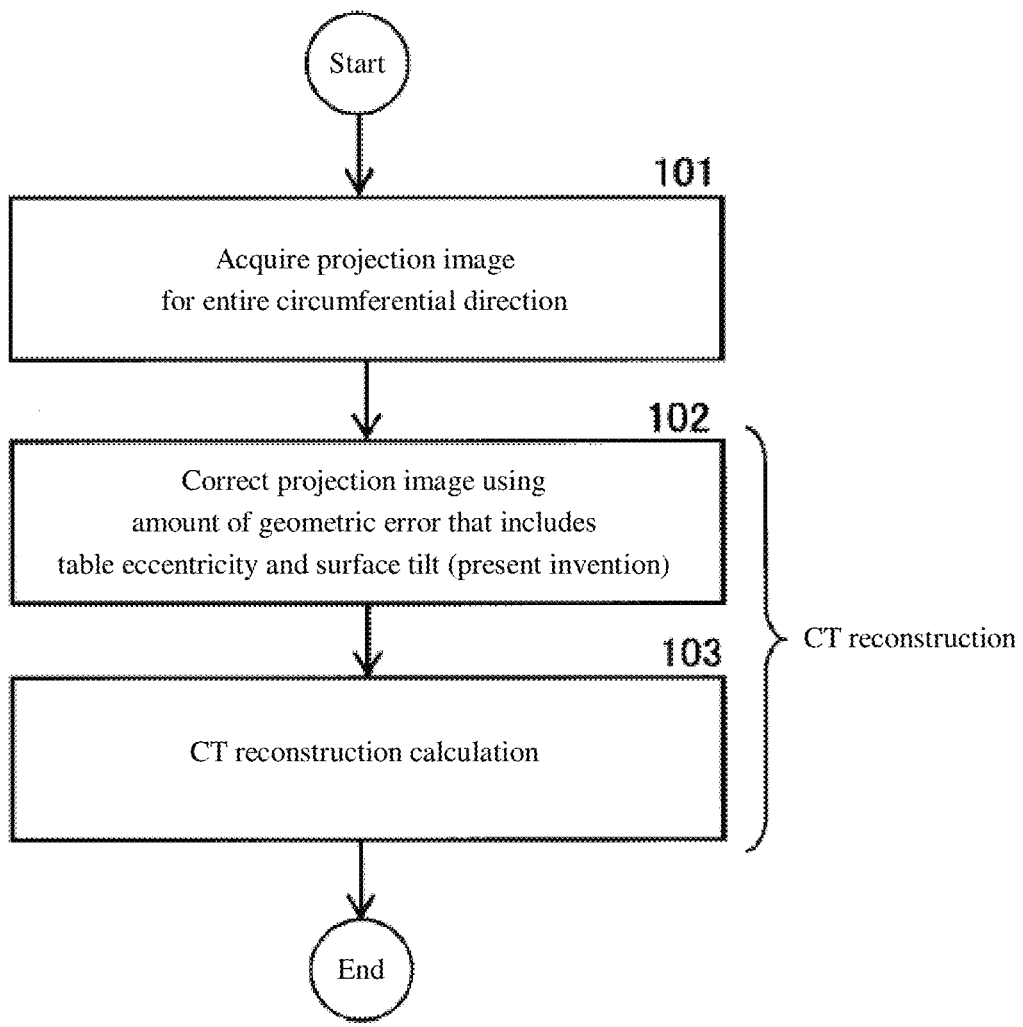
FIG. 10 is a flowchart illustrating a procedural flow according to a first embodiment of the present invention.

FIG. 10 illustrates a procedure of a first embodiment of a CT scan that includes correction of a projection image according to the present invention.

First, in step 101, a rotary table 16 that is bombarded by X-rays 13 and on which a specimen W is placed is rotated continuously at a fixed speed or intermittently by fixed step widths, and a projection image of the specimen W is acquired in the entire circumferential direction (a fixed interval).

Next, at the point of CT reconstruction, before using the projection image in the CT reconstruction calculation, in step 102, the projection image is corrected using a known amount of geometric error that includes table eccentricity and surface tilt.

Next, using the corrected projection image, in step 103, a CT reconstruction calculation is performed and volume data is generated.

A specific procedure of correcting the projection image in the aforementioned step 102 follows.

Figure 11:
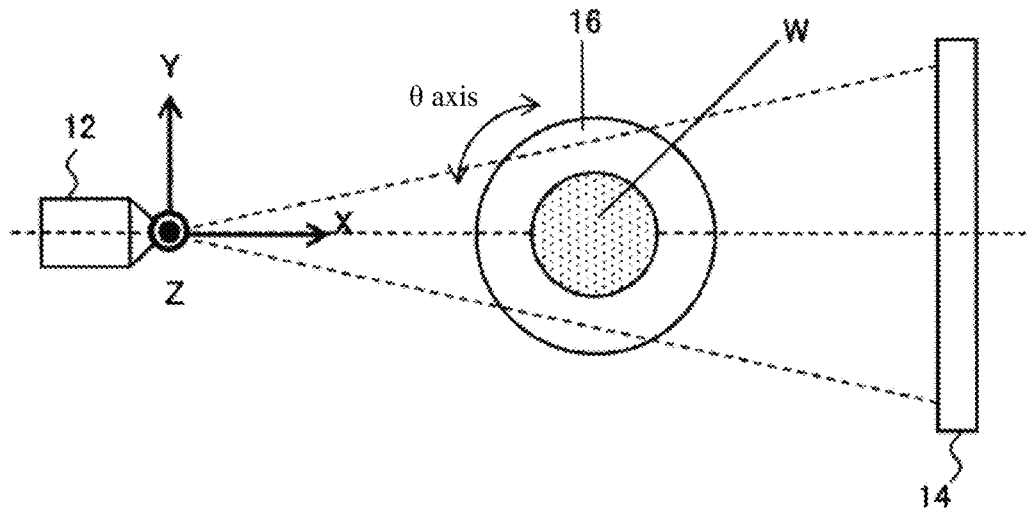
FIG. 11 is a plan view from above of the X-ray CT apparatus, providing the definition of a coordinate system used in the embodiment.
Figure 12:
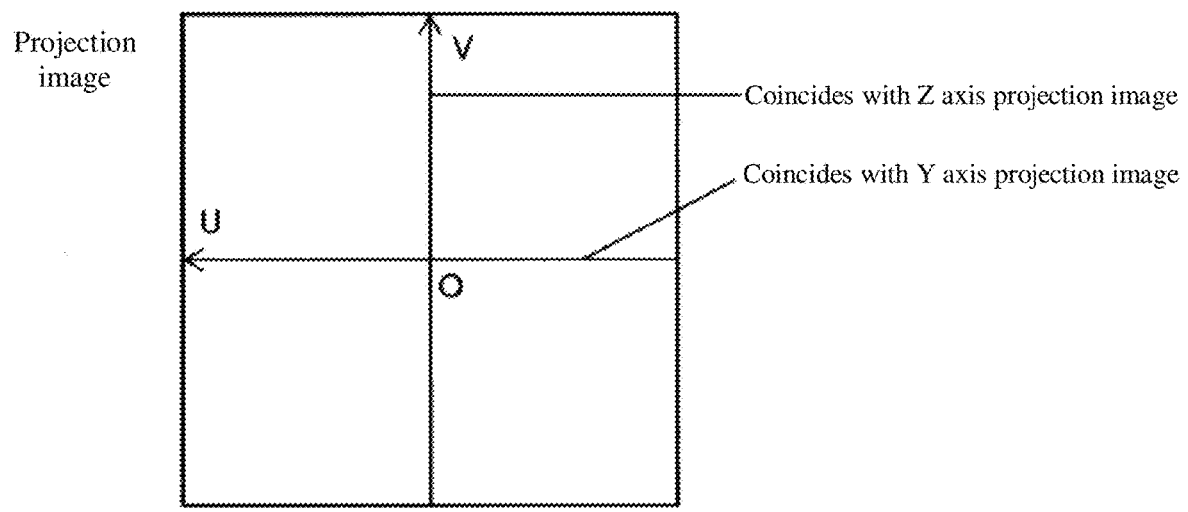
FIG. 12 is a lateral view providing the definition of a coordinate system on a projection image in the embodiment.

In this example, a coordinate system is defined in FIGS. 11 and 12 in order to describe the correction procedure.

Specifically, as illustrated in FIG. 11, for example, a coordinate system is defined with a position of an X-ray source 12 as the origin point, with an axis direction from the X-ray source 12 toward the X-ray detection device 14 as the X axis, with an axis that is in an upward direction and perpendicular to the surface of a rotary table 16 as the Z axis, and with an axis in a direction that is orthogonal to the X and Z as the Y axis.

As illustrated in FIG. 12, a coordinate system overlaid on the projection image is defined with the center of the projection image as an origin point O, with a horizontal direction axis as a U axis, and with a vertical direction axis as a V axis. The U axis coincides with the projection image of the Y axis while the V axis coincides with the projection image of the Z axis, and the orientations of each also respectively coincide.

Next, an example is described of acquiring an amount of geometric error for table eccentricity and surface tilt.

Figure 13:
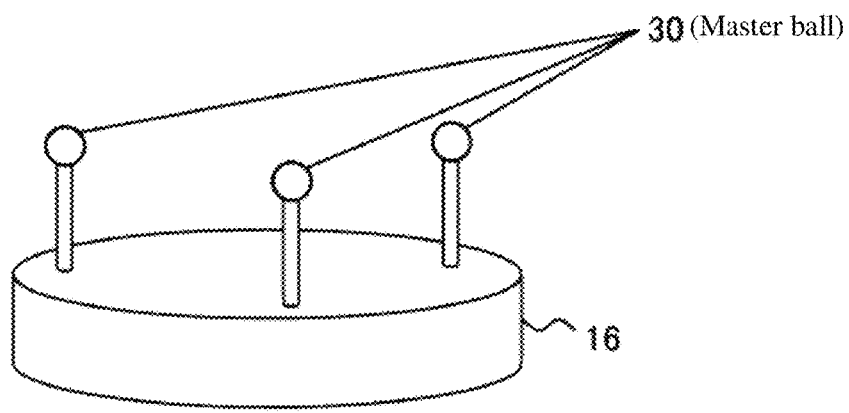
FIG. 13 is a perspective view illustrating an exemplary arrangement of master balls used to acquire an amount of geometric error in the embodiment.
Figure 14:
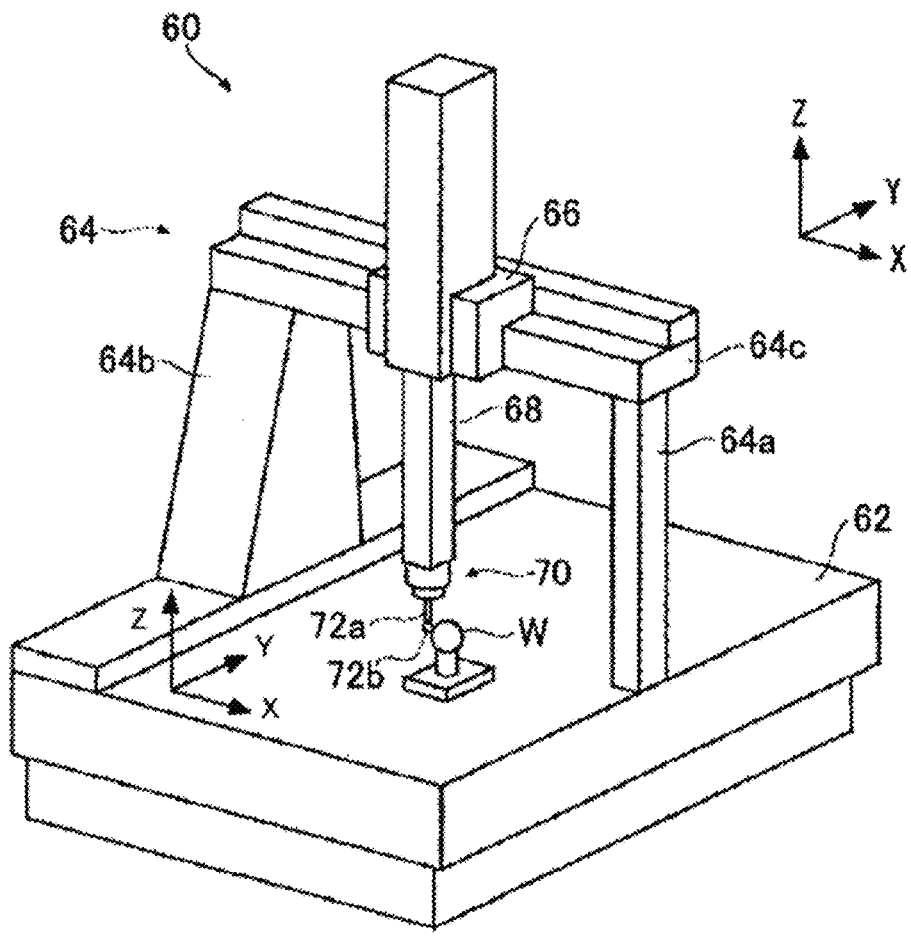
FIG. 14 is a perspective view of an exemplary coordinate measuring device in the embodiment.

When performing correction according to the present invention, acquiring an amount of geometric error for the eccentricity and surface tilt of the rotary table 16 before beginning is a prerequisite. As illustrated in FIG. 13, an acquisition method may be, for example, arranging a plurality (three are used in the drawing) of master balls 30 of equal height at positions an equal distance from the peripheral center of the rotary table 16 and performing a coordinate measurement of spatial positions of the master balls 30 for each constant pitch angle of the rotary table 16, using a coordinate measuring device 60 such as that illustrated in FIG. 14.

The coordinate measuring device 60 includes a surface plate 62 (reference plane); a portal frame 64 having a pair of support columns 64a and 64b which are movable on the surface plate 62 in a front-back direction (Y axis direction) and a beam 64c bridging over the support columns 64a and 64b; a movable column 66 which moves on the beam 64c of the portal frame 64 in a left-right direction (X axis direction); a movable slider 68 which moves on the column 66 in an up-down direction (Z axis direction); a probe 70 fixated to a bottom end of the slider 68; and a stylus 72a and, for example, a spherical stylus head 72b which are fixated to a tip (lower end in the drawing) of the probe 70.

Figure 15:
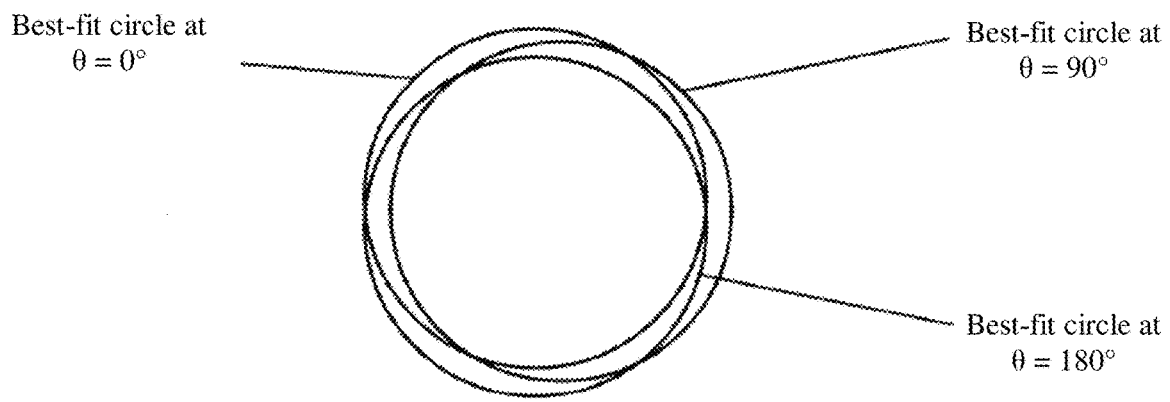
FIG. 15 is a plan view illustrating exemplary best-fit circles in the embodiment.

Specifically, the rotary table 16 is set at a given angle, and spatial positions of all the master balls 30 are found in this state using the coordinate measuring device 60. An example of a method for finding the spatial positions may include performing contact measurement of the location of each master ball 30 using the stylus head 72b of the coordinate measuring device 60, a best-fit sphere (sphere conformation) is found based on the obtained measurement points, and using the center thereof as the spatial position. In addition, a best-fit circle can be found using the spatial positions of the master balls 30 arranged on the periphery. As illustrated in FIG. 15, the rotary table 16 is rotated at a constant pitch angle and a plurality of these best-fit circles are obtained (in FIG. 15, there are three with θ=0°, 90°, and 180°), and by investigating changes in the positions, the eccentricity of the rotary table 16 can be calculated. In a case where there is no eccentricity, the positions of the best-fit circles calculated for each angle all coincide.

An example of a specific calculation method may be to first find a plane via plane fitting based on the spatial coordinates of each master ball 30 at a given angle. For example, when the spatial position of the $i^{th}$ master ball 30 at a given angle θ is represented as $P_{\theta i}$, the calculation may be performed as follows using the least square method.

[Formula 1]

$$P_{\theta i} = (x_{\theta i}, y_{\theta i}, z_{\theta i}) \quad (1)$$

$$ax + by + cz = d \text{ (Plane equation)} \quad (2)$$

$$\sum_i (ax_{\theta i} + by_{\theta i} + cz_{\theta i} - d)^2 \rightarrow \quad (3)$$

min (Derive $a, b, c, d$ with least square method)

Next, the spatial position of each master ball 30 is projected onto this plane and the best-fit circle on the plane is found, and a center position $C_\theta$ of the circle is calculated. A new two-dimensional coordinate system (composed of the U axis and V axis, for example) is created for the plane, and when a planar position projected onto the plane is represented as $P_{\theta i}'$, the calculation may be performed as follows using the least square method.

[Formula 2]

$$P'_{\theta i} = (u_{\theta i}, v_{\theta i}) \quad (4)$$

-continued $$(u - Cu)^2 + (v - Cv)^2 = r^2 \quad \text{(Circle equation)} \tag{5}$$

$$\sum_i \{(u_{\theta i} - Cu)^2 + (v_{\theta i} - Cv)^2 - r^2\}^2 \rightarrow \tag{6}$$

min (Derive $Cu$, $Cv$, $r$ with least square method)

Figure 16:
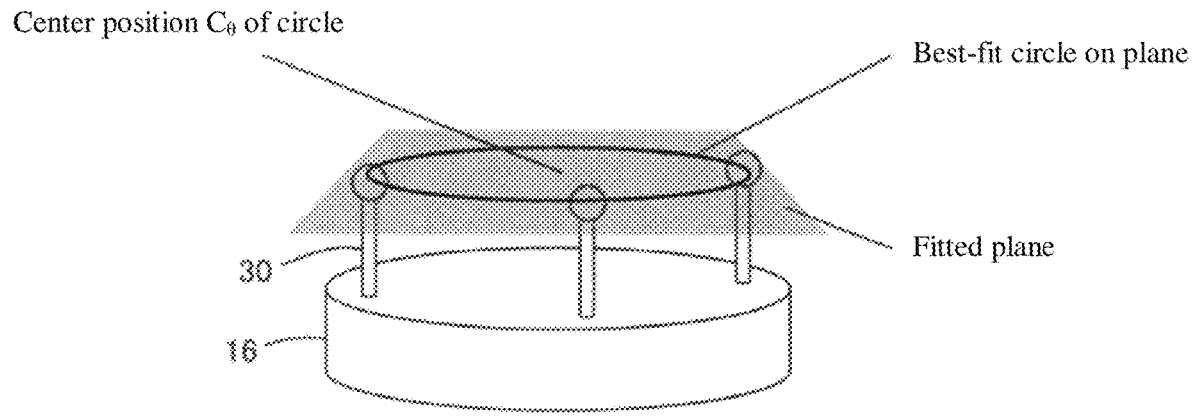
FIG. 16 is a perspective view illustrating a plane and a circle that have been fit to the rotary table in the embodiment.

The circle center ($Cu$, $Cv$) on the resulting plane is transformed into spatial coordinates and the center position $C_\theta$ of the circle as illustrated in FIG. 16 is found.

The calculations above are performed for each rotation angle and $C_\theta$ is calculated at all of the angles.

[Formula 3]

Next, a standard is established to calculate the eccentricity. When the standard is defined as an average $\overline{C_\theta}$ of each $C_\theta$, an amount of eccentricity Be can be represented as follows.

$$E_\theta = (e_x, e_y, e_z) = C_\theta - \overline{C_\theta} \tag{7}$$

As for a surface tilt $N_\theta$, a normal vector of the fitted plane is used at each angle.

$$N_\theta = (n_x, n_y, n_z) \tag{8}$$

This is merely one example of deriving the table eccentricity and surface tilt. A calibration tool other than the master balls 30 may also be used, and a measurement conducted by a tool other than the coordinate measuring device 60 may also be used (for example, detecting a change in position/inclination of a master ball 30 projected on a projection image).

Next, principles of applying the amount of geometric error for the eccentricity and surface tilt to the CT reconstruction to perform correction are described.

This example is described concretely using a back projection method of CT reconstruction.

CT reconstruction using a back projection method performs back projection at the same angle as when projecting a circumferential-direction projection image of the specimen W, and obtains volume data (or a sectional image). In this example, a parallel beam scan is described that is necessitated in consideration of the back projection method.

The parallel beam scan is a scanning method where, for each rotation angle of a CT scan, the X-ray source 12 moves parallel to the X-ray detection device 14 and X-rays 13 incident on the X-ray detection device 14 always intersect with the device orthogonally. The back projection method creates a back projection orthogonal to an image plane based on a projection image obtained by the X-ray detection device 14, and therefore constitutes the opposite principle to that of the parallel beam scan.

The CT reconstruction using the method of back projection of the parallel beam scan can be expressed as follows with a pixel value p of the projection image, a rotation angle $\theta$, and a pixel value $\mu$ of a sectional image.

[Formula 4]

$$\mu(x,y) = \int_0^\pi p(t,\theta) * h(t) d\theta \tag{9}$$

$$t = x \cos \theta + y \sin \theta \tag{10}$$

$$h(t) = \int_{-\infty}^\infty |f| e^{i 2\pi f t} df \tag{11}$$

Figure 17:
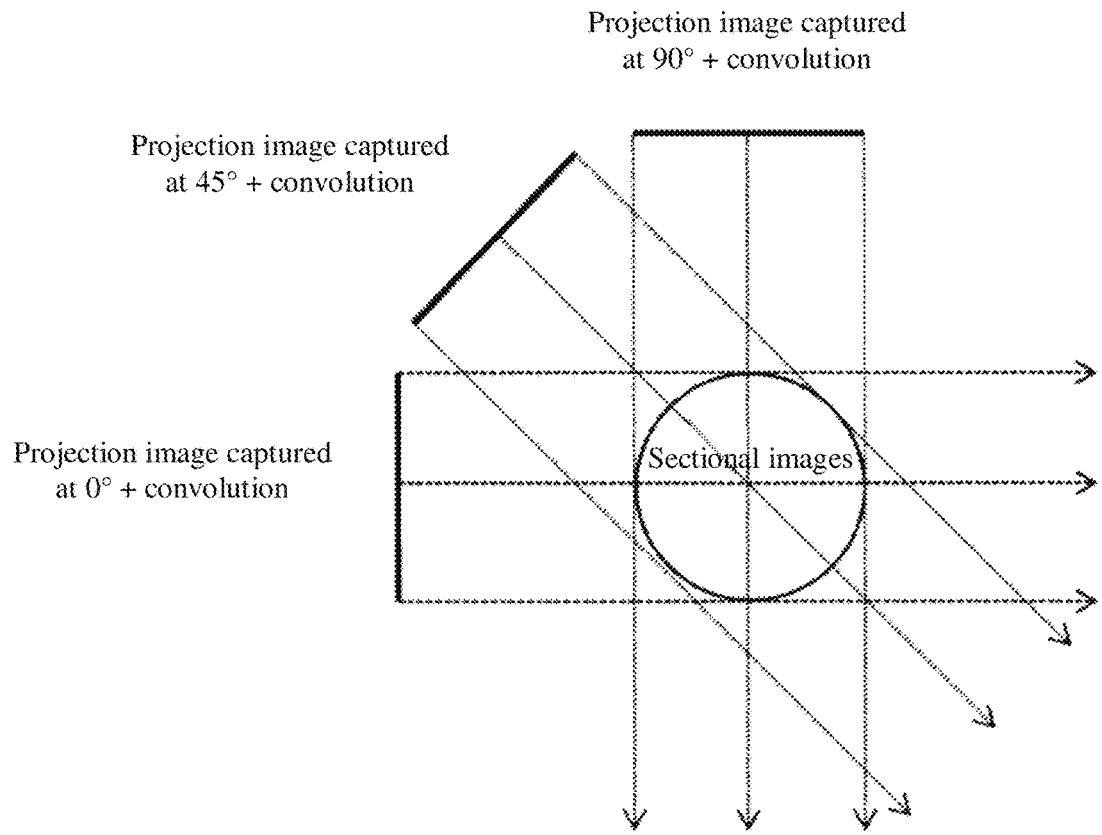
FIG. 17 is a plan diagram of a bird's-eye view of a back projection method in the embodiment.

The above formula expresses an integration of the pixel values while performing convolution (convolutional integration) on the projection images acquired at each angle, resulting in a processed image such as that illustrated in FIG. 17.

An exemplary condition for correctly performing CT reconstruction using the back projection method is to create a back projection of X-rays that have passed through a specimen interior during the CT scan, the back projection being created in the same position and direction as at the time of the scan.

Figure 18:
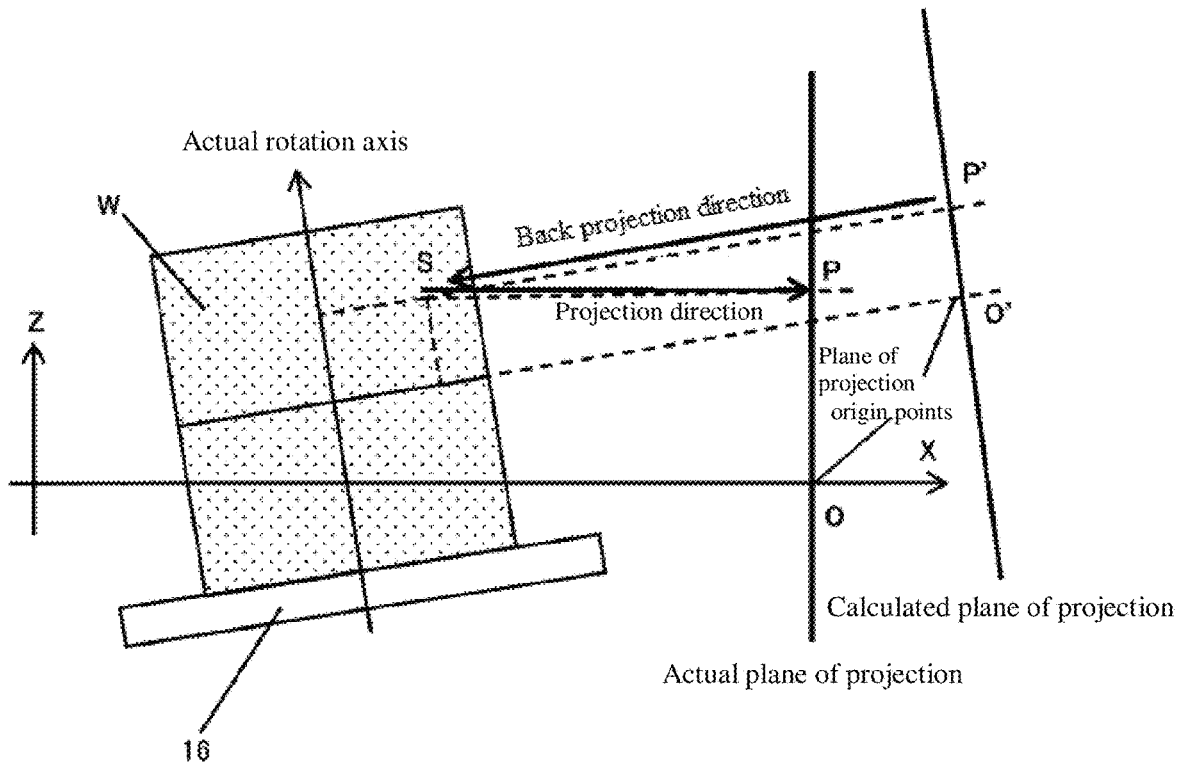
FIG. 18 is a lateral view illustrating a CT scan and back projection in the embodiment, as viewed from the side.

Next, concrete effects of back projection are described for a case where the rotary table has eccentricity and surface tilt. FIG. 18 shows a CT scan and back projection, as viewed from the side.

The rotary table 16 has eccentricity and surface tilt, and the rotation axis of the specimen W is not parallel to the plane of projection. Meanwhile, with the back projection calculation, a back projection is created with respect to a plane of projection that is parallel to the rotation axis, and when placed in physical space, the calculated plane of projection is as illustrated in FIG. 18.

Focusing now on a single point S within the specimen W, the point S is projected and the position on the plane of projection at which the point S is projected is designated as P, and the position of the projection image used in the back projection calculation is designated as P'. In this example, this results in a CT reconstruction error.

In the present invention, during CT reconstruction the posture of the calculated plane of projection is corrected to the posture of the actual plane of projection, and accordingly pixels in the projection images manipulated during projection and back projection are configured to be identical, and the back projection calculation is performed correctly.

Even with a scanning method other than the parallel beam scan, ordinarily the calculation is performed by converting to a parallel beam during the back projection calculation. Accordingly, by further generalizing and simplifying the calculation formula for the parallel beam scan described previously, the formula may be expressed as follows.

[Formula 5]

$$\mu(x,y,z) = \int_0^{2\pi} p(u,v,\theta) * h(u,v) d\theta \tag{12}$$

In the actual calculation, back projection must be performed as each individual scanning method is calculated. However, in the description of the correction according to the present example, any fundamental formula that convolves the projection image and back projects the image in the circumferential direction suffices. Therefore, the above expression (12) is used.

In the following, the correction procedure of step 102 shown in FIG. 10 is described with reference to FIG. 19.

First, in step 1021, a back projection calculation formula that incorporates the correction is derived.

As noted above, the CT reconstruction is corrected by transforming the posture of the projection image in the CT reconstruction to the actual posture.

Strictly speaking, such correction is a process in which the pixel positions of the projection image referenced by the back projection calculation of the CT reconstruction are transformed into correct pixel positions.

Figure 20:
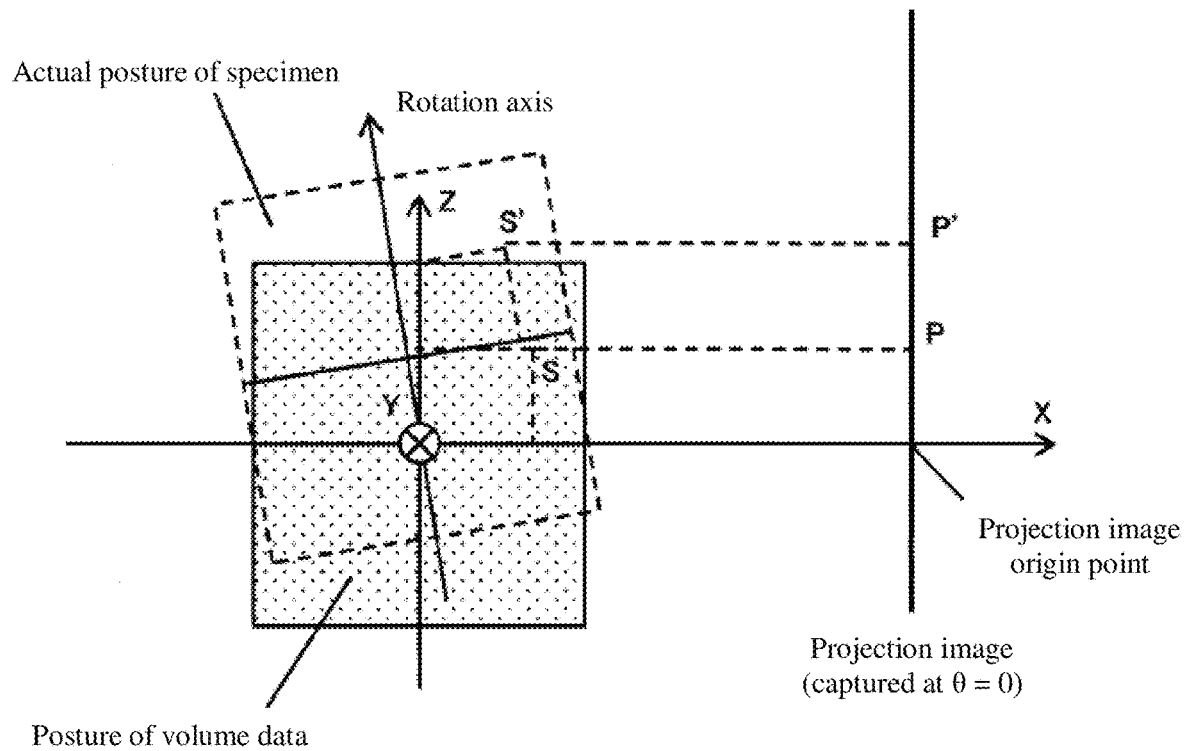
FIG. 20 is a lateral view illustrating how volume data is generated with a back projection calculation of a CT reconstruction in the embodiment.

FIG. 20 illustrates how volume data is generated with the back projection calculation of the CT reconstruction. In order to more easily illustrate this, the volume data and the projection image are arranged on the same coordinate system as the spatial coordinate system described above. The volume data center is arranged on the origin point of the coordinate system, and a projection image acquired when a rotation angle $\theta$ at the time of the CT scan is 0° is arranged in a posture that is orthogonal to the X axis.

In this example, reconstruction of a given point S (x, y, z) in the volume data is considered. The position P of the point S on the projection image can be illustrated as follows, due to the U axis in the projection image being parallel to the Y axis, the V axis being parallel to the Z axis, and the X axis passing through the origin point of the projection image (using the coordinate system defined for the projection image).

[Formula 6]

$$p(u, v) = \begin{bmatrix} y \\ z \end{bmatrix} \quad (13)$$

When expanded so as to enable correspondence with the projection images acquired at each angle θ, in view of the fact that the position P rotates in space about the Z axis, the position P can be expressed as follows.

[Formula 7]

$$p(u, v) = \begin{bmatrix} -x\sin\theta + y\cos\theta \\ z \end{bmatrix} \quad (14)$$

The reconstruction of the point S is calculated using the pixel value for the position P on the projection image, but due to the effects of eccentricity and surface tilt, the pixel value for the position P does not include projection data for the point S. To find a position on the projection image that includes the projection data for the point S, the actual posture of the specimen W is conformed to the above figure, resulting in a position P' where a point S' that occupies the same position on the specimen as the point S is projected. In other words, in the reconstruction of the point S, the pixels of the position P' may be used rather than those of the position P.

When a matrix that transforms the volume data and the posture of the specimen W is designated as $M_\theta$ (derivation procedure is described below), the position P' can be found as follows.

[Formula 8]

$$S'(x', y', z') = M_\theta S \quad (15)$$

$$P' = \begin{bmatrix} -x'\sin\theta + y'\cos\theta \\ z' \end{bmatrix} \quad (16)$$

In this example, the posture transformation matrix $M_\theta$ can be found as follows.

The posture of the specimen W is the same as the posture of the rotary table 16, and therefore is offset by an eccentricity $E_\theta$ and has a slope of a surface tilt vector $N_\theta$. First, consider a case where the specimen W is restored to an original posture. In restoring the specimen W to the original posture, the posture of the specimen W is offset in the opposite direction by an amount of eccentricity, and so is rotated to align the surface tilt vector with the Z axis (because the surface tilt vector is the same as the Z axis when there is no surface tilt).

Figure 21A:
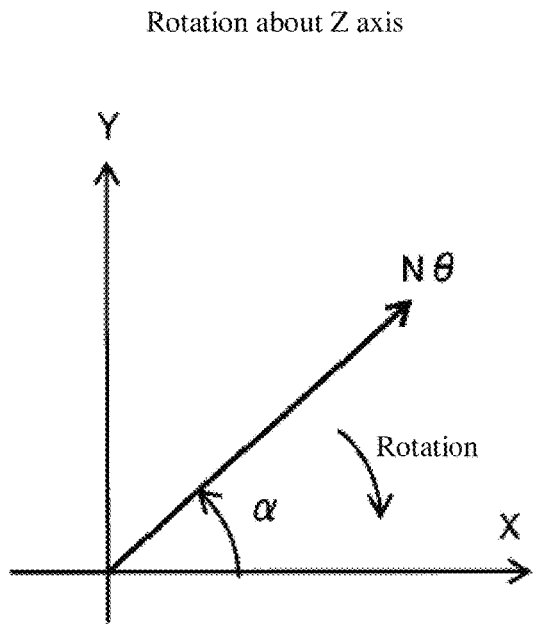
FIGS. 21A and 21B illustrate rotation methods in the embodiment.
Figure 21B:
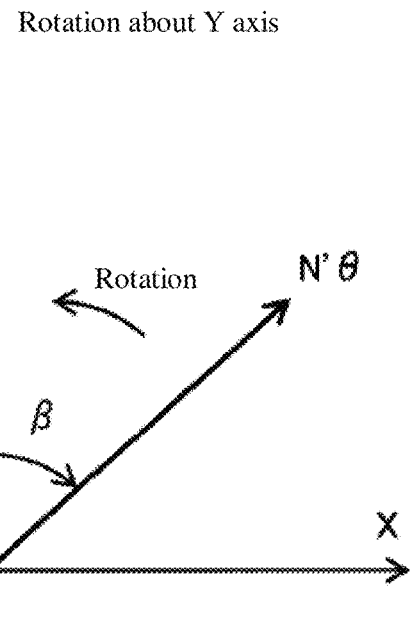

In this example, the rotation method is to rotate, in order, (A) about the Z axis and (B) about the Y axis, as illustrated in FIGS. 21A and 21B.

[Formula 9]

$$\cos\alpha = \frac{n_x}{\sqrt{n_x^2 + n_y^2}} \quad (17)$$

$$\cos\beta = \frac{\sqrt{n_x^2 + n_y^2}}{\sqrt{n_x^2 + n_y^2 + n_z^2}} \quad (18)$$

At first, rotation about the Z axis, illustrated in FIG. 21A, places the surface tilt vector $N_\theta$ on an XZ plane and the transformed vector is designated as $N'_\theta$. Next, rotation about the Y axis, illustrated in FIG. 21B, causes the vector $N'_\theta$ to coincide with the Z axis.

The transformation that restores the posture in this way performs reverse eccentricity offset, Z axis rotation, and Y axis rotation in that order, and therefore reverse transformation of the posture transformation matrix $M_\theta$ can be performed by inverting this order. The posture transformation matrix $M_\theta$ is shown below.

[Formula 10]

$$M_\theta = \begin{bmatrix} 1 & 0 & 0 & e_x \\ 0 & 1 & 0 & e_y \\ 0 & 0 & 1 & e_z \\ 0 & 0 & 0 & 1 \end{bmatrix} \begin{bmatrix} \cos\alpha & -\sin\alpha & 0 & 0 \\ \sin\alpha & \cos\alpha & 0 & 0 \\ 0 & 0 & 1 & 0 \\ 0 & 0 & 0 & 1 \end{bmatrix} \begin{bmatrix} \cos\beta & 0 & \sin\beta & 0 \\ 0 & 1 & 0 & 0 \\ -\sin\beta & 0 & \cos\beta & 0 \\ 0 & 0 & 0 & 1 \end{bmatrix} \quad (19)$$

In light of the above description, a back projection calculation formula that incorporates corrections utilizing the amount of geometric error for the table eccentricity and surface tilt is as follows.

[Formula 11]

$$\mu(x, y, z) = \int_0^{2\pi} p(u', v', \theta) * h(u', v') d\theta \quad (20)$$

$$\begin{bmatrix} u' \\ v' \end{bmatrix} = \begin{bmatrix} -x'\sin\theta + y'\cos\theta \\ z' \end{bmatrix} \quad (21)$$

$$\begin{bmatrix} x' \\ y' \\ z' \\ 1 \end{bmatrix} = M_\theta \begin{bmatrix} x \\ y \\ z \\ 1 \end{bmatrix} \quad (22)$$

Normally, the positions μ' and v' on the projection image are not integers, and therefore when referencing the pixel value at p(μ', v', θ), a suitable pixel value must be obtained through linear interpolation or the like.

Figure 19:
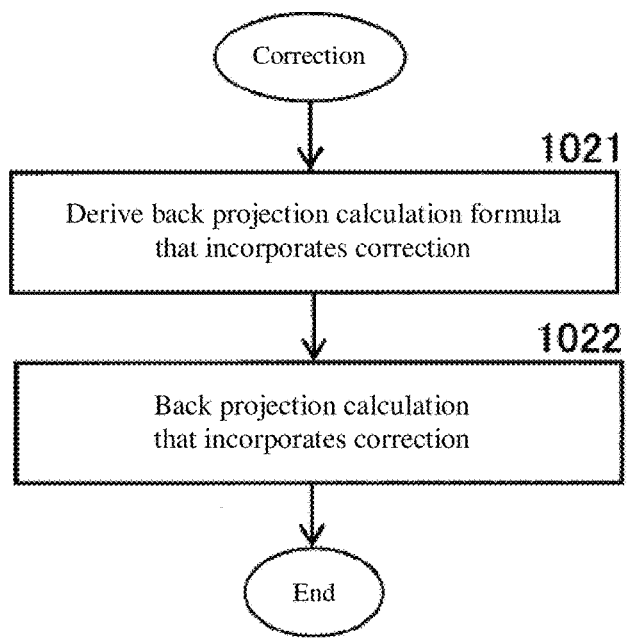
FIG. 19 is a flowchart illustrating a correction procedure in the embodiment.

Next, proceeding to step 1022 of FIG. 19, a back projection calculation is performed using the back projection calculation formula found in step 1021 above in order to perform correction.

For example, in a procedure where each pixel of the volume data is completed one at a time, the back projection calculation formula obtained in step 1021 may be applied to bring in a desired pixel from the projection images for each angle.

In such a case, the posture transformation matrix Me, which is dependent on the angle θ, must be prepared ahead of time for all angles.

In addition, in a procedure where back projection is performed on each of the projection images for each angle in turn and the volume data is constructed incrementally, this is essentially equivalent to correcting the projection images for each angle and then performing a normal back projection calculation. The relationships of the pixel positions before and after correction are understood as noted below, and therefore the projection image can be corrected.

[Formula 12]

$$\begin{bmatrix} u \\ z \end{bmatrix} = \begin{bmatrix} -x\sin\theta + y\cos\theta \\ z \end{bmatrix} \quad (23)$$

$$\begin{bmatrix} u' \\ v' \end{bmatrix} = \begin{bmatrix} -x'\sin\theta + y'\cos\theta \\ z' \end{bmatrix} \quad (24)$$

$$\begin{bmatrix} x' \\ y' \\ z' \\ 1 \end{bmatrix} = M_\theta \begin{bmatrix} x \\ y \\ z \\ 1 \end{bmatrix} \quad (25)$$

Figure 22:
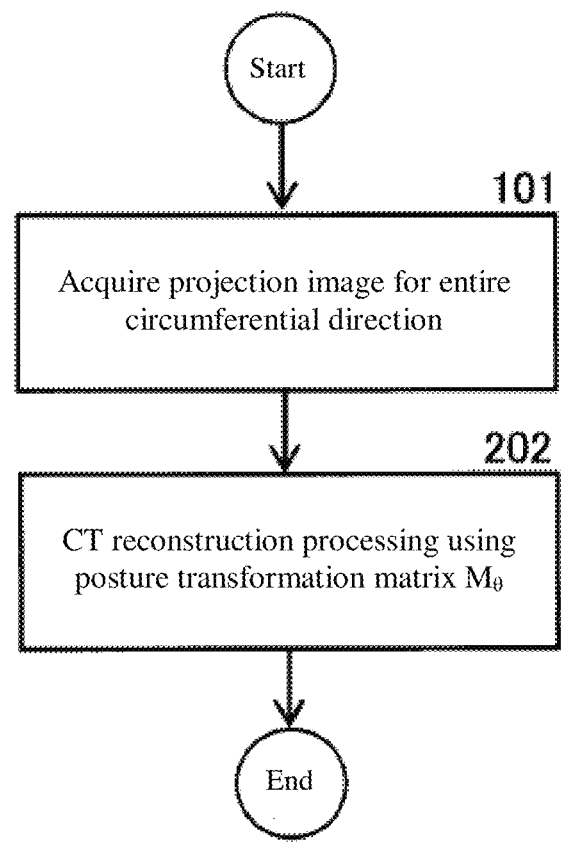
FIG. 22 is a flowchart illustrating a procedural flow according to a second embodiment of the present invention.

FIG. 22 illustrates a procedural flow according to a second embodiment of the present invention, where steps 102 and 103 of the first embodiment illustrated in FIG. 10 are integrated.

In the present embodiment, after a step 101 similar to that of the first embodiment ends, in step 202, a reconstruction process is performed using the posture transformation matrix Me illustrated in expression (19) above.

In the present embodiment, the posture transformation matrix Me is applied to a CT reconstruction process, and therefore processing is quick and easy.

In the embodiment described above, an example using a back projection method is given, but the correction method using the amount of geometric error to the projected image can also be applied to other reconstruction methods (for example, successive reconstruction), as well.

In addition, the present invention is not limited to a geometric error for the eccentricity or surface tilt of a rotary table. If a known amount of geometric error can be expressed in a transformation matrix (the posture transformation matrix Me described above), any sort of geometric error can be corrected.

Figure 1:
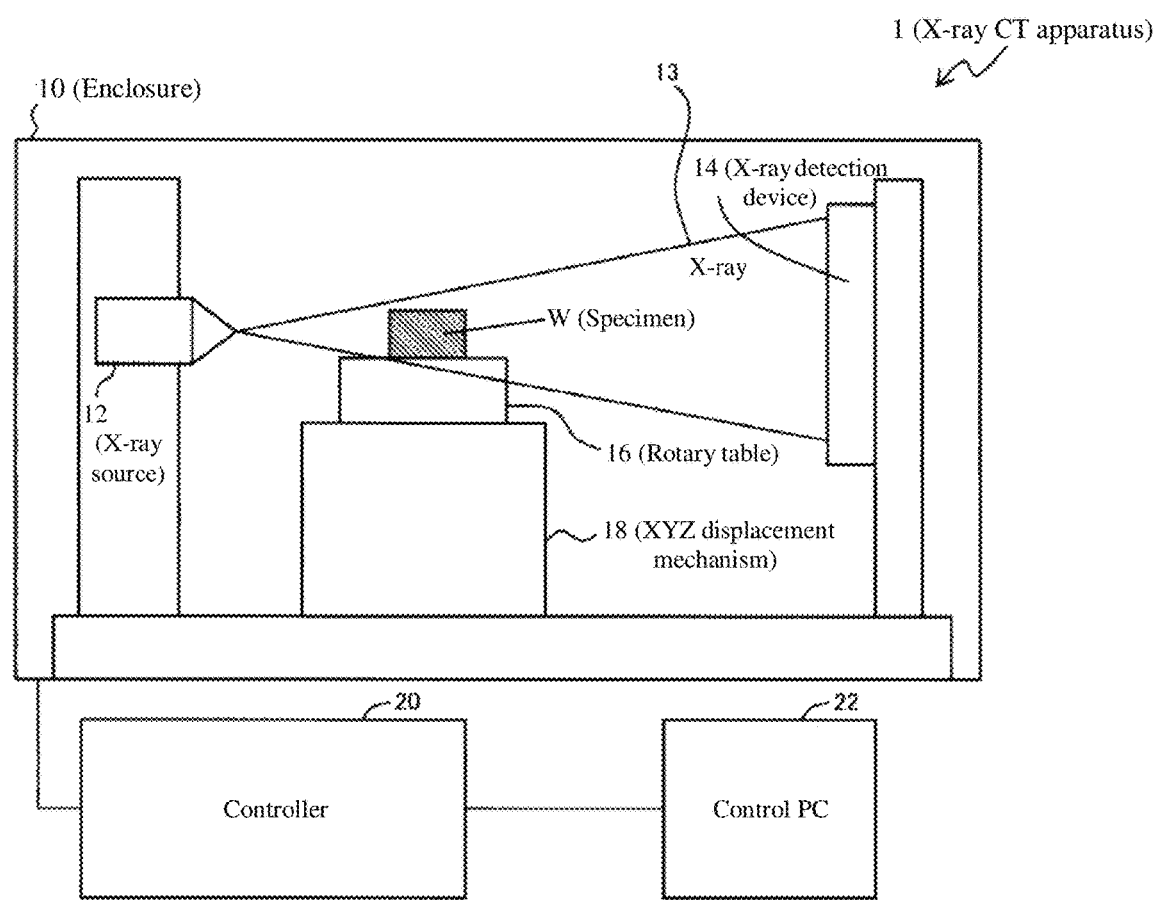
FIG. 1 illustrates a cross section of an overall configuration of a generic X-ray CT apparatus used for measurement.
Figure 2:
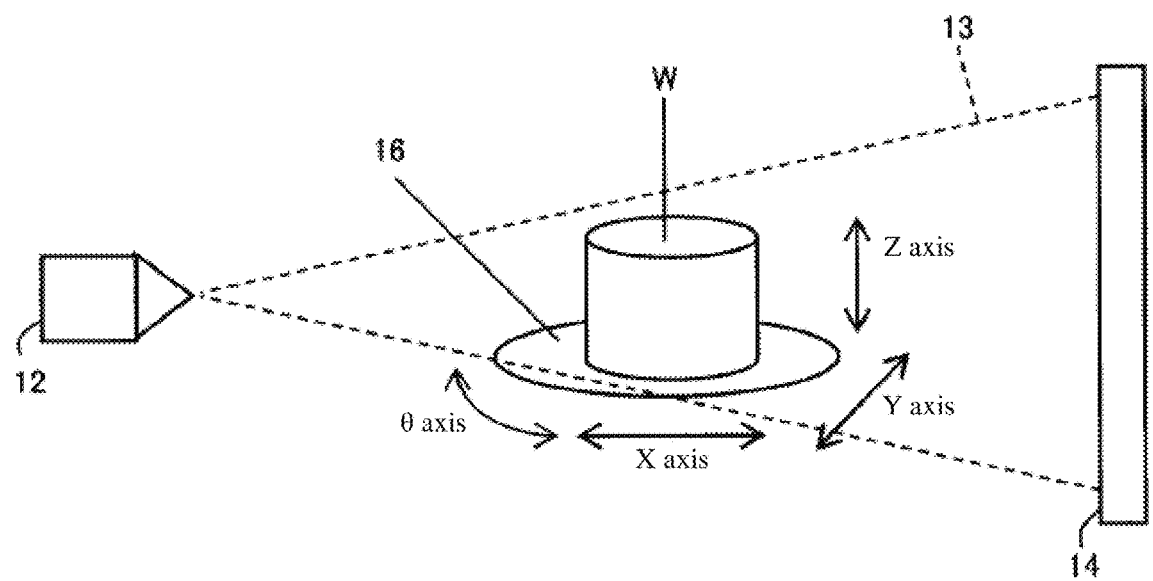
FIG. 2 is a perspective view showing an arrangement of relevant portions of the generic X-ray CT apparatus used for measurement.
Figure 3:
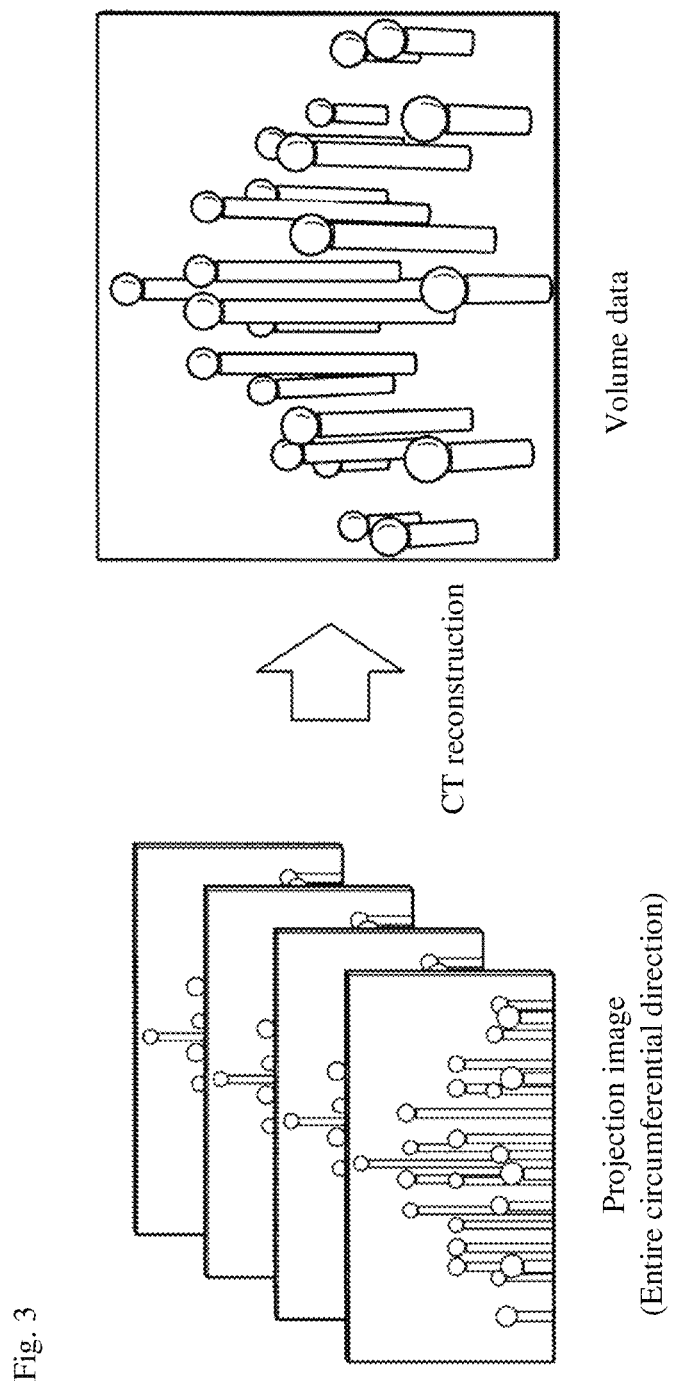
FIG. 3 illustrates an overview of CT reconstruction.
Figure 4:
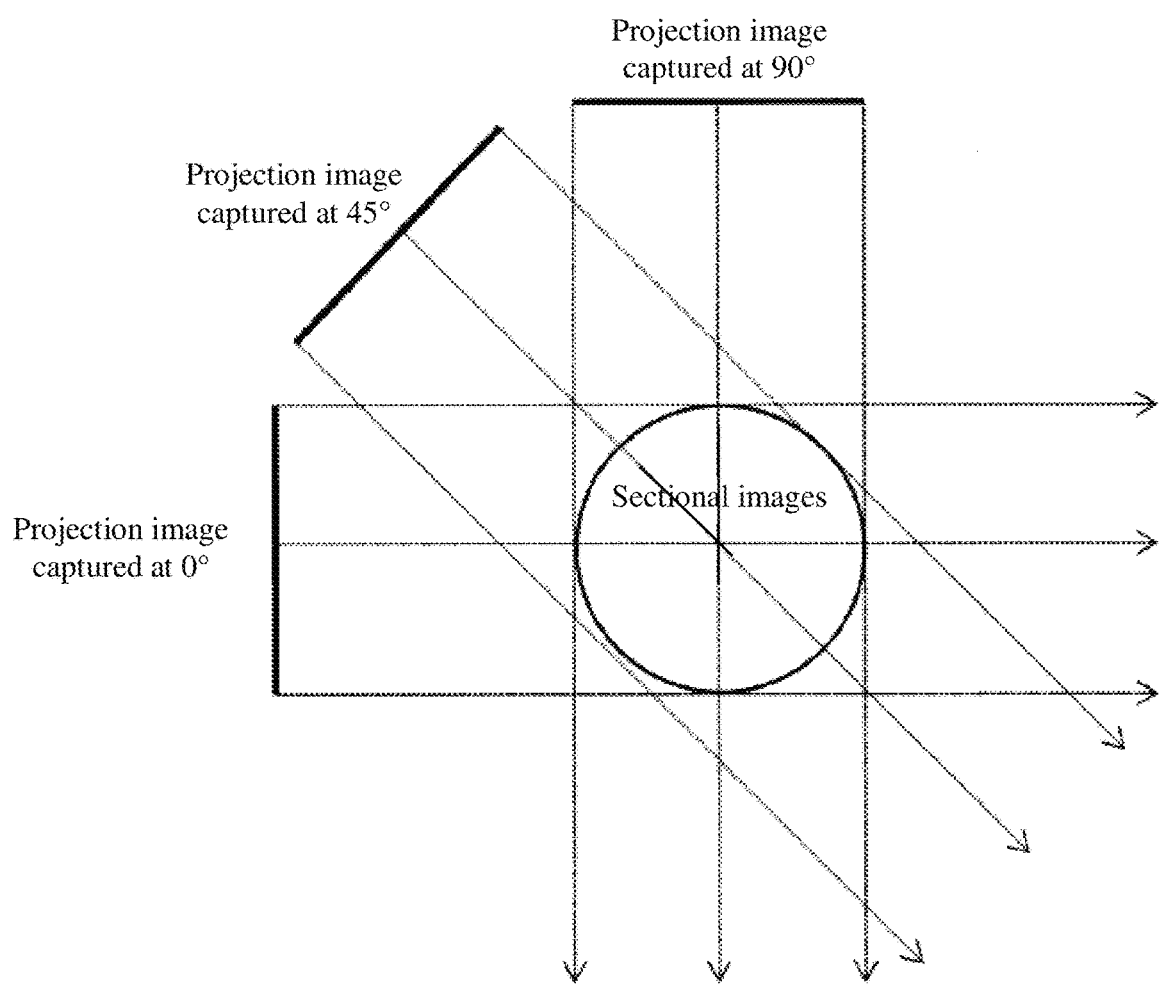
FIG. 4 illustrates an overview of a back projection method.
Figure 5:
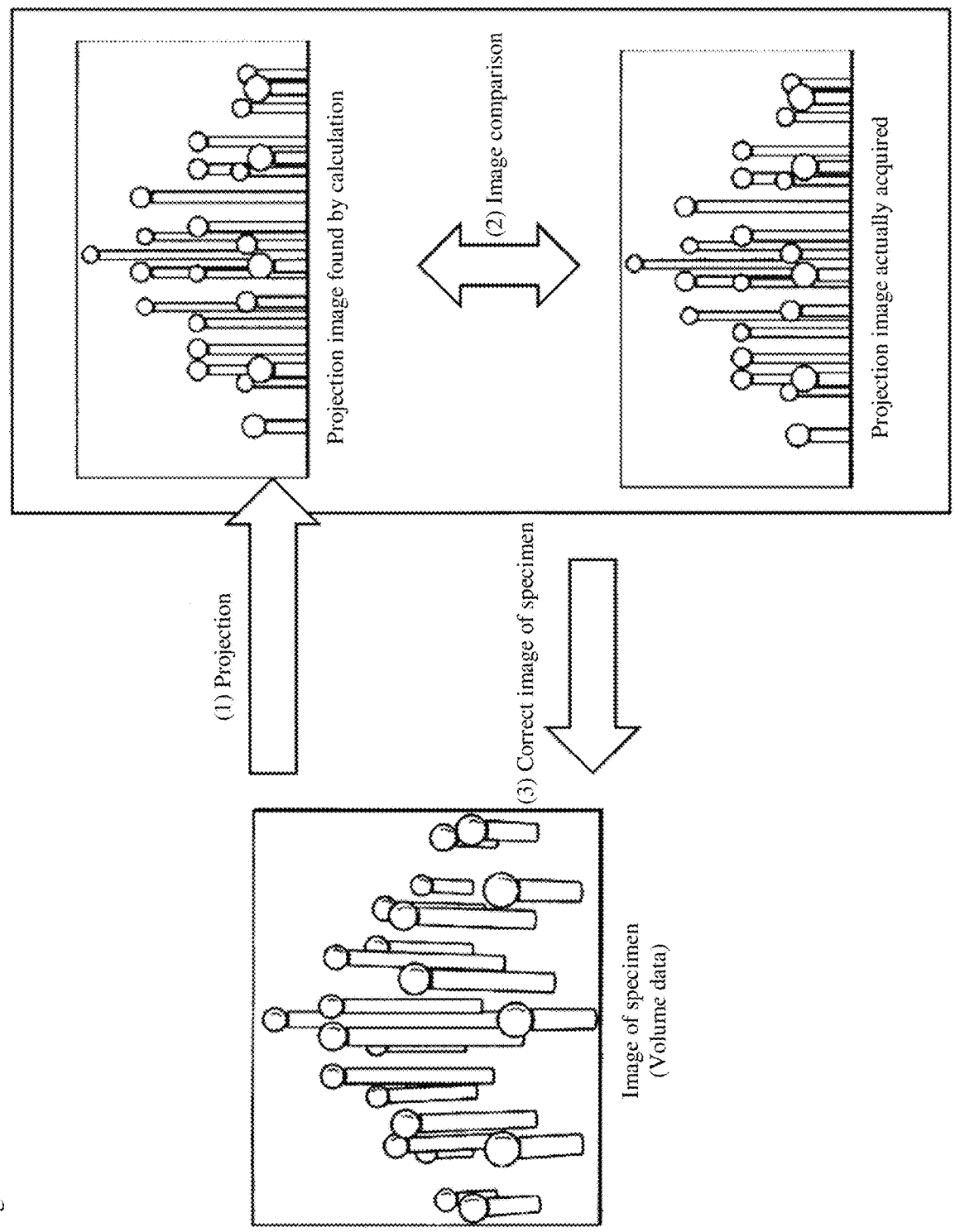
FIG. 5 illustrates an overview of a successive approximation method.
Figure 6:
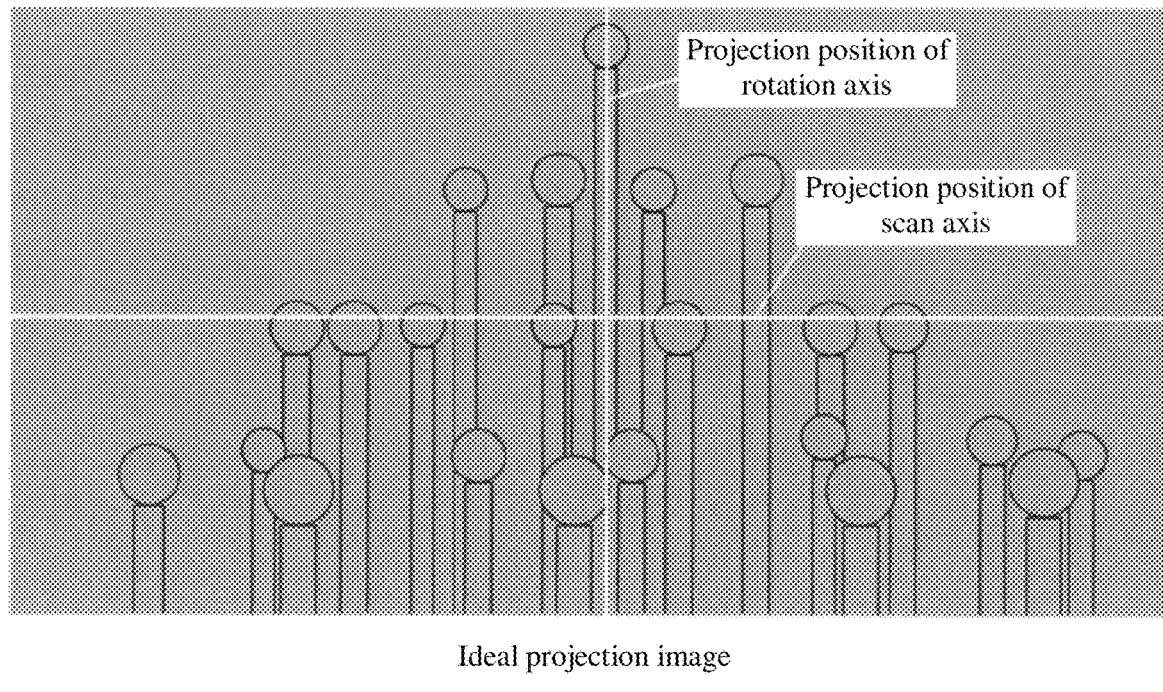
FIG. 6 illustrates an example of an ideal projection image.
Figure 7:
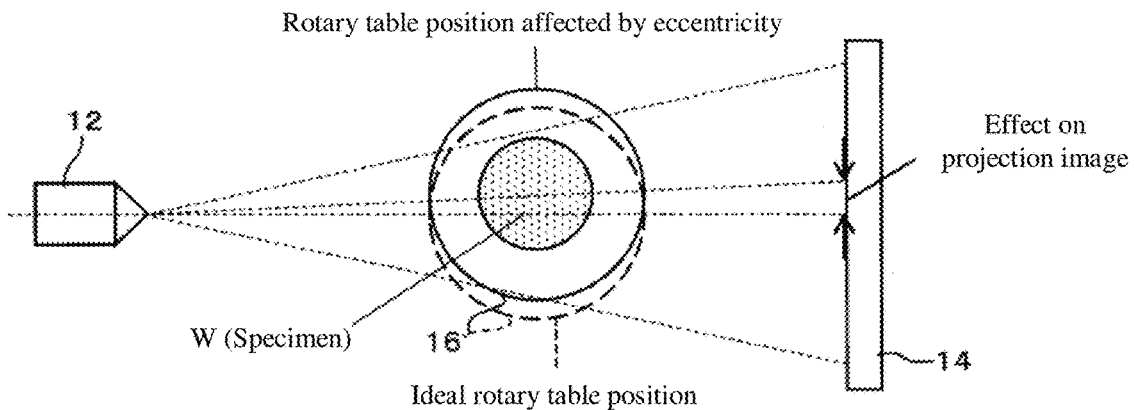
FIG. 7 is a plan view of relevant portions of an X-ray CT apparatus illustrating eccentricity of a rotary table.
Figure 8:
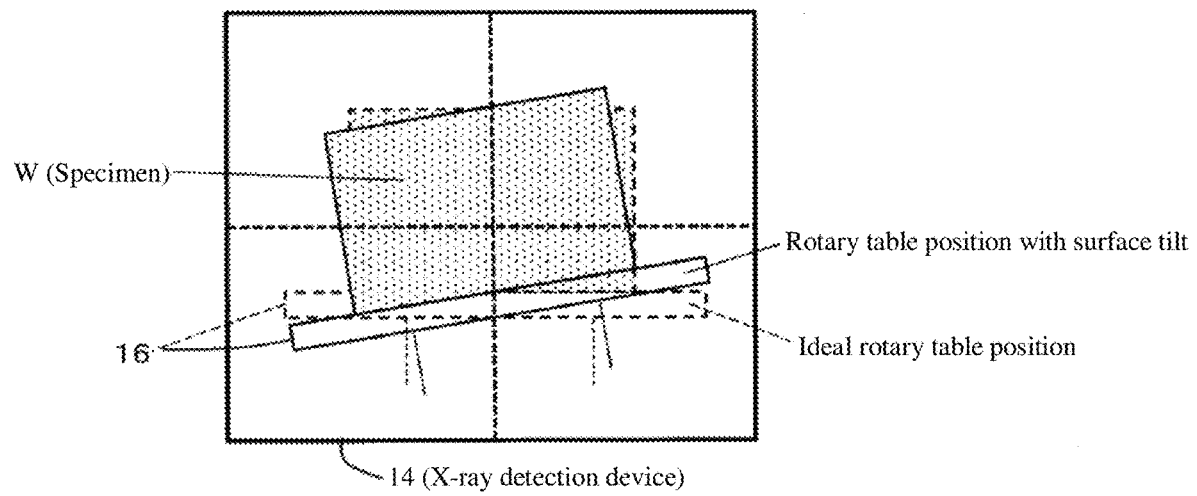
FIG. 8 is a lateral view illustrating a state of a specimen and an X-ray detection device viewed from an X-ray source in the X-ray CT apparatus that illustrates a surface tilt of the rotary table.
Figure 9:
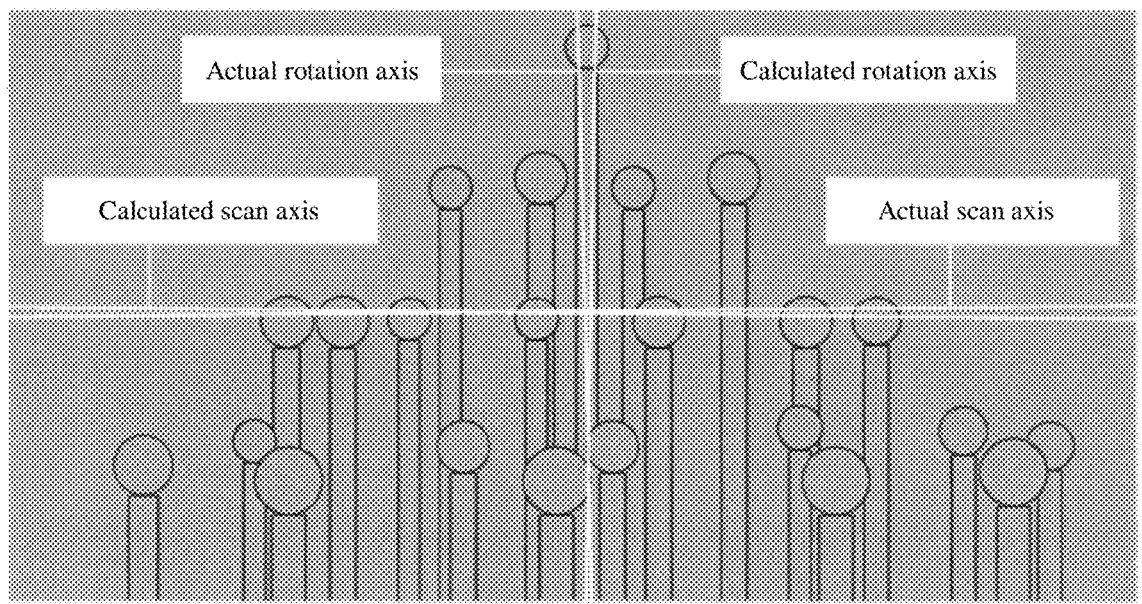
FIG. 9 illustrates an exemplary projection image for a case where the rotary table has eccentricity and surface tilt.

As illustrated in FIG. 1, the control PC 22 may include at least one processor. The processor is tangible and non-transitory. As used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. The processor is an article of manufacture and/or a machine component. The processor is configured to execute software instructions in order to perform functions as described in the various embodiments herein. For example, the processor is configured to execute instructions such that the processor operates as a corrector that uses the stored amount of geometric error to correct the projection image, and a reconstructor that uses the corrected projection image to reconstruct a tomographic image.

The processor may be a general purpose processor or may be part of an application specific integrated circuit (ASIC). The processor may also be a microprocessor, a microcomputer, a processor chip, a controller, a microcontroller, a digital signal processor (DSP), a state machine, or a programmable logic device. The processor may also be a logical circuit, including a programmable gate array (PGA) such as a field programmable gate array (FPGA), or another type of circuit that includes discrete gate and/or transistor logic. The processor may be a central processing unit (CPU), a graphics processing unit (GPU), or both. Additionally, any processor described herein may include multiple processors, parallel processors, or both. Multiple processors may be included in, or coupled to, a single device or multiple devices.

The control PC 22 may also include one or more computer memories. The computer memory may include a static memory, a dynamic memory, or both in communication. Memories described herein are tangible storage mediums that can store data and executable instructions, and are non-transitory during the time instructions are stored therein. Again, as used herein, the term "non-transitory" is to be interpreted not as an eternal characteristic of a state, but as a characteristic of a state that will last for a period of time. The term "non-transitory" specifically disavows fleeting characteristics such as characteristics of a particular carrier wave or signal or other forms that exist only transitorily in any place at any time. The memories are an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a cache, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted. Of course, the computer memory may include any combination of memories or a single storage.

The control PC 22 may also include a medium reader which is configured to read any one or more sets of instructions, e.g. software, from any of the memories described herein. The instructions, when executed by a processor, can be used to perform one or more of the methods and processes as described herein. In a particular embodiment, the instructions may reside completely, or at least partially, within the memory, the medium reader, and/or the processor during execution by the control PC 22.

The control PC 22 is shown in FIG. 1 as a personal computer. However, those skilled in the art appreciate that, in alternative embodiments of the present application, the control PC 22 may be a laptop computer, a tablet PC, a personal digital assistant, a mobile device, a palmtop computer, a desktop computer, a communications device, a wireless telephone, a personal trusted device, a web appliance, a server, a security camera, or any other device that is capable of executing a set of instructions, sequential or otherwise, that specify actions to be taken by that device. Of course, those skilled in the art appreciate that the above-listed devices are merely exemplary devices and that the control PC 22 may be any additional device or apparatus commonly known and understood in the art without departing from the scope of the present application. Furthermore, those skilled in the art similarly understand that the device may be any combination of devices and apparatuses.

Of course, those skilled in the art appreciate that the above-listed components of the control PC 22 are merely meant to be exemplary and are not intended to be exhaustive and/or inclusive. Furthermore, the examples of the components listed above are also meant to be exemplary and similarly are not meant to be exhaustive and/or inclusive.

In accordance with various embodiments of the present disclosure, the methods described herein may be implemented using a hardware computer system that executes software programs. Further, in an exemplary, non-limiting embodiment, implementations can include distributed processing, component/object distributed processing, and parallel processing. Virtual computer system processing can be constructed to implement one or more of the methods or functionality as described herein, and a processor described herein may be used to support a virtual processing environment.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A measuring X-ray CT apparatus that is configured to emit X-rays while rotating a specimen that is arranged on a rotary table and to reconstruct a projection image thereof to generate a tomographic image of the specimen, the measuring X-ray CT apparatus comprising:
   one or more memories that store:
   a set of executable instructions, and
   an amount of geometric error that is obtained prior to the specimen being arranged on the rotary table, and that is included in the projection image, the amount of geometric error being either or both of eccentricity and surface tilt of the rotary table;
   a processor, which when executing the set of executable instructions, is configured to operate as:
   a corrector that uses the stored amount of geometric error to correct the projection image; and
   a reconstructor that uses the corrected projection image to reconstruct a tomographic image.

2. A tomographic image generating method for a measuring X-ray CT apparatus which, when generating a tomographic image, emits X-rays while rotating a specimen that is arranged on a rotary table, and reconstructs a projection image thereof to generate a tomographic image of the specimen, the method comprising:
   obtaining and storing, prior to the specimen being arranged on the rotary table, an amount of geometric error that is included in the projection image, the amount of geometric error being either or both of eccentricity and surface tilt of the rotary table;
   using the stored amount of geometric error to correct the projection image; and
   using the corrected projection image to reconstruct a tomographic image.

3. The measuring X-ray CT apparatus according to claim 1, wherein the amount of geometric error is eccentricity and surface tilt of the rotary table.

4. The tomographic image generating method according to claim 2, wherein the amount of geometric error is eccentricity and surface tilt of the rotary table.

5. The measuring X-ray CT apparatus according to claim 1, wherein the eccentricity is a deviation by the rotary table from an ideal rotational axis and an actual rotational axis.

6. The tomographic image generating method according to claim 2, wherein the eccentricity is a deviation by the rotary table from an ideal rotational axis and an actual rotational axis.

* * * * *